(12) United States Patent
Harada et al.

(10) Patent No.: US 11,346,871 B2
(45) Date of Patent: May 31, 2022

(54) SENSOR (71) Applicant: NABTESCO CORPORATION, Tokyo (JP)

(72) Inventors: Masaki Harada, Tokyo (JP); Kazuhiko Sakurai, Tokyo (JP); Takashi Wada, Kobe (JP)

(73) Assignee: NABTESCO CORPORATION, Tokyo (JP)

( * ) Notice: Subject to any disclaimer, the term of this patent is extended or adjusted under 35 U.S.C. 154(b) by 0 days.

(21) Appl. No.: 17/035,440

(22) Filed: Sep. 28, 2020

(65) Prior Publication Data
US 2021/0132126 A1     May 6, 2021

(30) Foreign Application Priority Data
Nov. 5, 2019 (JP) .............................. JP2019-200714

(51) Int. Cl.
*G01R 27/16*     (2006.01)
*G01N 33/28*     (2006.01)

(52) U.S. Cl.
CPC ......... *G01R 27/16* (2013.01); *G01N 33/2858* (2013.01)

(58) Field of Classification Search
CPC ............. G01N 27/025; G01N 33/2858; G01N 2015/0053; G01N 15/0606; G01N 27/07; G01N 15/0656; G01N 27/043; G01N 2001/2826; G01R 27/08; G01R 27/16; B25J 19/0062; B25J 9/1674; B25J 19/02; B25J 9/102; F16N 9/00; F16H 57/0405
USPC ........................................................ 324/713
See application file for complete search history.

(56) References Cited

U.S. PATENT DOCUMENTS

| | | | |
|---|---|---|---|
| 5,179,346 A * | 1/1993 | McGee | G01N 15/0656 324/204 |
| 2006/0125487 A1* | 6/2006 | Itomi | G01N 33/2888 324/533 |
| 2017/0335944 A1* | 11/2017 | Nishimura | F16H 57/082 |
| 2018/0223907 A1 | 8/2018 | Ito et al. | |

(Continued)

FOREIGN PATENT DOCUMENTS

| | | | |
|---|---|---|---|
| DE | 102013212696 A1 * | 12/2014 | ......... G01N 33/2858 |
| EP | 3623803 A2 | 3/2020 | |

(Continued)

OTHER PUBLICATIONS

Extended European Search Report dated Mar. 15, 2021, issued in corresponding European Patent Application No. 20198378.0 (11 pgs.).

*Primary Examiner* — Tung X Nguyen
*Assistant Examiner* — Robert P Alejnikov, Jr.
(74) *Attorney, Agent, or Firm* — Pillsbury Winthrop Shaw Pittman, LLP (57) ABSTRACT

A sensor relating to the present invention includes: a first electrode; a second electrode; a first attracting portion positioned between the first electrode and the second electrode and configured to receive conductive abrasion powder contained in a detection region and attracted onto the first attracting portion; a sensing unit for sensing a change in electrical resistance between the first electrode and the second electrode caused by the conductive abrasion powder; and at least one second attracting portion positioned within the detection region and configured to attract the conductive abrasion powder contained in the detection region.

13 Claims, 6 Drawing Sheets

(56) References Cited

U.S. PATENT DOCUMENTS

2018/0275083 A1\* 9/2018 Kiriyama ............... G01N 27/12
2019/0154608 A1   5/2019 Nakamura et al.

FOREIGN PATENT DOCUMENTS

JP   2002-286697 A   10/2002
JP   2005-331324 A   12/2005

\* cited by examiner

SENSOR

CROSS-REFERENCE TO RELATED APPLICATIONS

This application is based on and claims the benefit of priority from Japanese Patent Application Serial No. 2019-200714 (filed on Nov. 5, 2019), the contents of which are hereby incorporated by reference in their entirety.

TECHNICAL FIELD

The present invention relates to a sensor.

BACKGROUND

A mechanical device such as a speed reducer is housed in a housing filled with a lubricating oil in order to prevent the mechanical parts such as gears from being damaged. If the mechanical parts are worn out during operation of the mechanical device, abrasion powder (for example, a conductive substance such as iron powder) is mixed into the lubricating oil. The abrasion powder is, for example, of a conductive substance such as iron powder. As the mechanical parts are increasingly worn out and enter a wear-out failure period, which is defined in a failure rate curve (a bathtub curve), an increased amount of abrasion powder is mixed into the lubricating oil. For this reason, a sensor for sensing the amount of the abrasion powder in the lubricating oil can be used for accurate preventive maintenance of the mechanical parts.

For example, Japanese Patent Application Publication No. 2002-286697 discloses an oil check sensor, which can be used for the above purposes. The disclosed oil check sensor is mounted to, for example, a transmission of an automobile and configured to check, for example, deterioration of an oil in an oil container and the degree of wear of mechanical parts lubricated with the oil. This sensor includes a pair of electrodes and a magnet for attracting iron powder or the like (a conductive substance) contained in the oil. Based on the resistance between the electrodes, which depends on the conductive substance attracted, the sensor senses the amount of the conductive substance in the oil.

The abrasion powder to be detected in the speed reducer or the like first increases due to initial wear, then remains substantially constant during normal operation and finally suddenly increases before occurrence of failures. This increase in the amount of the abrasion power before failures can be sensed with a known conventional sensor. However, the conventional sensor may malfunction when a large amount of abrasion powder is produced due to initial wear, for example, when the speed reducer has a large size. If such is the case, the sensor may not be capable of sensing the increase in the amount of the abrasion powder before the occurrence of failures, which is originally intended to be sensed. There is also a demand for prevention of sensor malfunction and thereby detection of failures in advance in order to reliably suspend and replace the speed reducer and the like.

Furthermore, while the mechanical device such as a speed reducer is manufactured, foreign matter having a large particle size (for example, a cutting chip or the like) generated by cutting or other methods of processing may adhere to the constituent components of the mechanical device and get mixed in with the lubricating oil. If such foreign matter having a large particle size adheres to the sensor, a short circuit occurs between the paired electrodes even with little abrasion powder produced. For the reasons stated above, the sensor for sensing the amount of abrasion powder may operate unexpectedly even when a small amount of abrasion powder is produced.

SUMMARY

The present invention is made in light of the above, and aims to achieve an object of providing a sensor that can be prevented from operating unexpectedly due to foreign matter mixed in and a difference found between the amount of abrasion powder produced and the designated amount to trigger the operation.

A sensor relating to one aspect of the present invention comprises: a first electrode; a second electrode; a first attracting portion positioned between the first electrode and the second electrode and configured to receive conductive abrasion powder contained in a detection region and attracted onto the first attracting portion; a sensing unit for sensing a change in electrical resistance between the first electrode and the second electrode caused by the conductive abrasion powder; and at least one second attracting portion positioned within the detection region and configured to attract the conductive abrasion powder contained in the detection region.

In this sensor, the conductive abrasion powder attracted between the first electrode and the second electrode causes a short circuit between the first electrode and the second electrode or a change in electrical resistance between the first electrode and the second electrode. This enables the sensing unit to sense the amount of the conductive abrasion powder in the detection region. In addition, the second attracting portion attracts the conductive abrasion powder in the detection region. This adjusts a short circuit or a change in electrical resistance between the first electrode and the second electrode with respect to the amount of the conductive abrasion powder in the detection region, making it possible to prevent the sensor from operating unexpectedly.

In the sensor related to one aspect of the present invention, the at least one second attracting portion may be spaced apart from the first electrode, the second electrode, and the first attracting portion.

The sensor related to one aspect of the present invention may comprise a sensitivity adjusting unit for adjusting attraction of the conductive abrasion powder to change sensitivity, wherein the at least one second attracting portion may comprise a plurality of second attracting portions having different attractive powers for attracting the conductive abrasion powder, and wherein the sensitivity adjusting unit may be formed of the plurality of second attracting portions.

A sensor related to one aspect of the present invention comprises: an outer electrode shaped like a tube having a bottom portion; an insulator arranged within the outer electrode, the insulator being an internal tube having a bottom portion; a first magnet arranged within the insulator; an inner electrode arranged within the insulator, the inner electrode being closer to an opening of the outer electrode in an axial direction than the first magnet is; a sensing unit for sensing attraction of conductive abrasion powder causing a change in electrical resistance between the outer electrode and the inner electrode; and a second magnet arranged outside the outer electrode and configured to attract the conductive abrasion powder.

In the sensor relating to one aspect of the present invention, a separate magnet forming the sensitivity adjusting unit adjusts attraction of the conductive abrasion powder. With this configuration, even when a large amount of abrasion powder is attracted, the sensitivity of the sensor can be adjusted depending on the attraction of the conductive abrasion powder, so that the sensing can be reliably performed. In particular, when the sensor is placed in a large-size speed reducer or the like and a large amount of abrasion powder is thus produced by initial wear, the sensor can be configured such that the attraction of the initial abrasion powder is limited or the sensing scheme is changed if a large amount of abrasion powder is attracted. This enables the sensor to reliably perform the sensing.

In this way, when a large amount of conductive abrasion powder is expected to be produced, a second attracting portion having a high attractive power can be selected such that a smaller amount of conductive abrasion powder is attracted between the electrodes, thereby setting the sensitivity of the sensor at a predetermined level. On the other hand, when a small amount of conductive abrasion powder is expected to be produced, a second attracting portion having a low attractive power can be selected such that a larger amount of conductive abrasion powder is attracted between the electrodes, thereby setting the sensitivity of the sensor at a predetermined level.

The sensor relating to one aspect of the present invention may comprise: a first electrode; and a second electrode, wherein the first magnet may form a magnetic flux line between the first electrode and the second electrode.

Further, the sensitivity adjusting unit can include a separate magnet (a separate attracting portion, a second magnet) provided outside the outer electrode. In this case, the separate magnet can be selected from a group of separate magnets capable of attracting different amounts of abrasion powder, or the separate magnet can be omitted. An appropriate one can selected from the separate attracting portions having different attractive powers, such that the sensitivity of the sensor can be set at a predetermined level in accordance with an expected amount of conductive abrasion powder to be produced.

In this way, depending on the expected amount of conductive abrasion powder to be produced, a separate magnet is employed to attract the abrasion powder. This can reduce the amount of the abrasion powder to be attracted between the electrodes to set the sensitivity of the sensor at a predetermined level. Specifically, when a large amount of conductive abrasion powder is expected to be produced, a separate magnet having a strong magnetic force or a large size is selected. This reduces the amount of the abrasion powder to be attracted between the electrodes, thereby setting the sensitivity of the sensor at a predetermined level. On the other hand, when a small amount of conductive abrasion powder is expected to be produced, a separate magnet having a weak magnetic force or a small size is selected, or no separate magnet is provided. This allows a predetermined amount of abrasion powder to be attracted between the electrodes, thereby setting the sensitivity of the sensor at a predetermined level. In the sensor related to one aspect of the present invention, the separate magnet may be spaced apart in the detection region.

Advantageous Effects

The present invention can produce an effect of providing a sensor that can be prevented from operating unexpectedly and thus achieve improved reliability.

DESCRIPTION OF THE EMBODIMENTS

The following describes a first embodiment of a sensor relating to the present invention with reference to the drawings. Elements common to a plurality of drawings are denoted by the same reference signs throughout the plurality of drawings. For convenience of explanation, the drawings are not necessarily drawn to scale.

Figure 1:
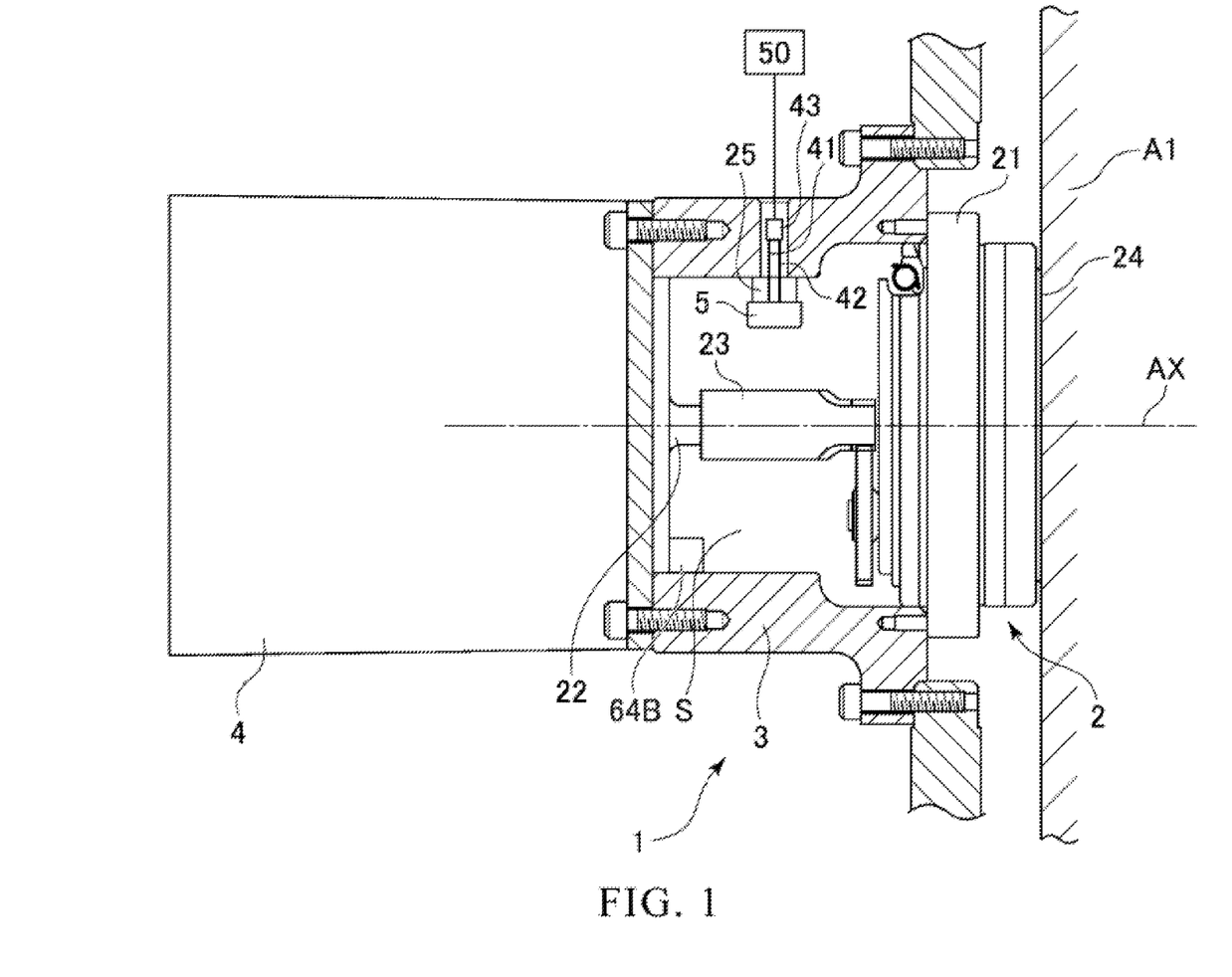
FIG. 1 is a sectional view showing one example of a mechanical device including a sensor relating to a first embodiment of the present invention.

FIG. 1 is a sectional view showing one example of a mechanism 1 including a sensor 5 relating to one embodiment of the present invention. The mechanism 1 is, for example, a movable part of a robot arm. The mechanism 1 includes a speed reducer 2, a flange 3 provided on the input side, a servomotor 4, and a device A1 provided on the output side.

The speed reducer 2 includes a casing 21 mounted to the flange 3, an input shaft 23 connected to an output shaft 22 of the servomotor 4, and an output shaft 24 connected to the output-side device A1. The input shaft 23 and the output shaft 24 are supported to be capable of rotating about an axis AX relative to the casing 21. The output from the servomotor 4 is input to the speed reducer 2 via the input shaft 23, reduced by the speed reducer 2, and then transmitted to the output-side device A1 via the output shaft 24. Thus, the output-side device A1 and the flange 3 are capable of rotating relative to each other.

The flange 3 is a tubular member and houses therein at least a portion of the speed reducer 2. The servomotor 4 is mounted to the flange 3. An opening in one end of the flange 3 in a direction along the axis AX is closed by the speed reducer 2, and an opening in the other end is closed by the servomotor 4. Thus, the flange 3 has a tightly closed hollow portion (a space S) formed therein. The space S contains therein a lubricating oil, so that the flange 3 also serves as an oil bath.

The casing 21 of the speed reducer 2 houses therein a gear mechanism, for example. The space within the casing 21 communicates with the space S within the flange 3. As the speed reducer 2 operates, the gear mechanism in the casing 21 rotates, which subsequently causes the lubricating oil to circulate between the space in the casing 21 and the space S in the flange 3. As the lubricating oil circulates, a conductive substance such as abrasion powder (conductive abrasion powder) produced in the speed reducer 2 moves into the space S in the flange 3.

In the space S, a sensor 5 is installed for sensing the amount of the conductive substance contained in the lubricating oil. The sensor 5 is fixed onto the flange 3 via, for example, a support member 25. The sensor 5 uses a magnet to gather the conductive substance contained in the lubricating oil between paired electrodes and uses a change in electrical resistance between the paired electrodes to sense the amount of the conductive substance in the lubricating oil. The sensor 5 may be alternatively positioned, for example, inside the casing 21 but can be at any position within the space containing therein the lubricating oil in the mechanism 1. The detection region of the sensor 5 covers the region within which the lubricating oil circulates.

Figure 2A:
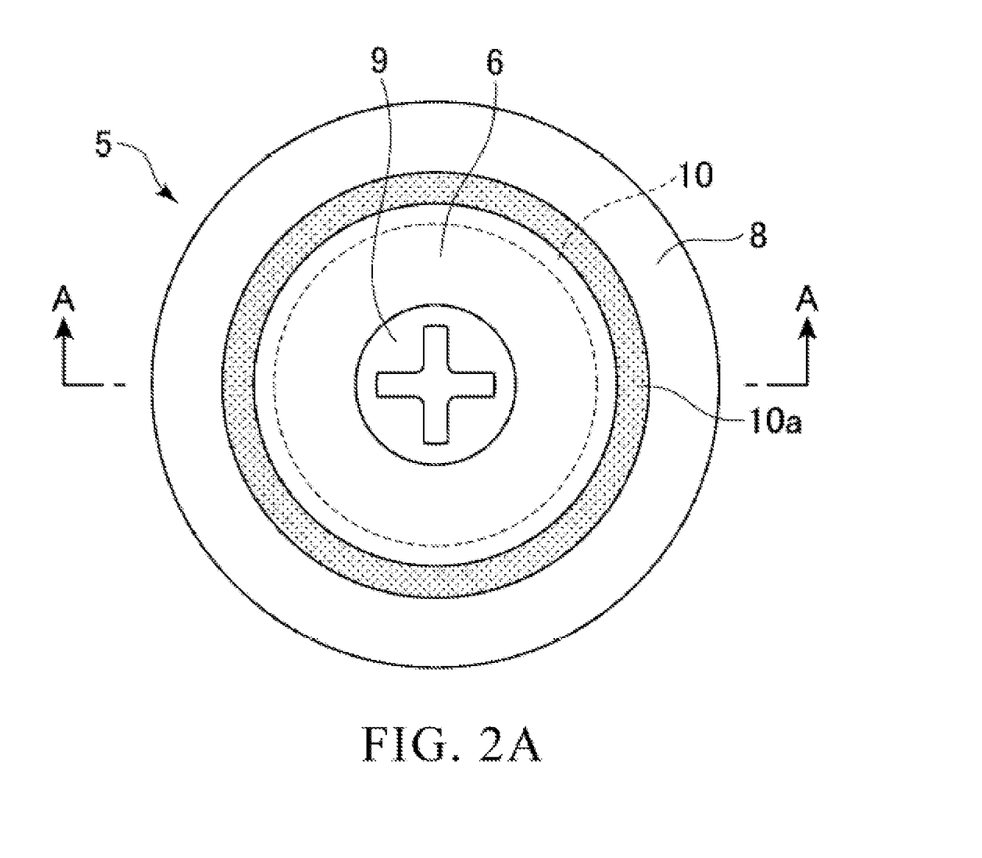
FIG. 2A is a top view of the sensor relating to the first embodiment of the present invention.
Figure 2B:
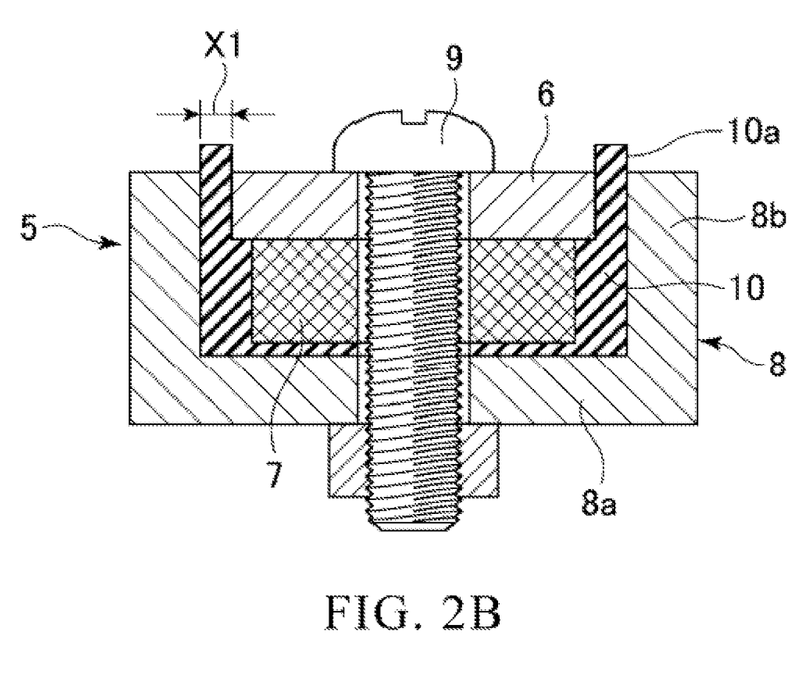
FIG. 2B is a sectional view of the sensor relating to the first embodiment of the present invention.

Next, with reference to FIGS. 2A to 2B, a detailed description is given of the structure of the sensor 5. FIG. 2A schematically shows the structure of the sensor relating to the first embodiment of the present invention. FIG. 2B shows a sectional view showing a cross-section of the sensor along the A-A line in FIG. 2.

As shown in FIGS. 2A to 2B, the sensor 5 has a substantially columnar outer shape and includes a first electrode 6, a magnet 7, a second electrode 8, a fastening member 9, an attracting portion 10 (a first attracting portion), and a separate magnet (a second attracting portion, a separate attracting portion) 64B (see FIG. 1). As shown in FIGS. 2A to 2B, the first electrode 6 has a circular shape when seen from above the top surface of the sensor 5 and is positioned at the center of the sensor 5. The second electrode 8 is a bottomed tubular member and includes a bottom portion 8a extending substantially parallel to the first electrode 6 and a wall portion (tubular portion) 8b continuous with the bottom portion 8a and extending substantially perpendicularly to the bottom portion 8a.

The magnet 7 has a substantially columnar shape and is positioned between the first electrode 6 and the bottom portion 8a of the second electrode 8. The first electrode 6, the magnet 7, and the bottom portion 8a of the second electrode 8 each have therein a through hole, through which the fastening member 9 (a bolt in the illustrated embodiment) is inserted. The fastening member 9 is inserted through the through holes, so that the first electrode 6, the magnet 7, and the second electrode 8 are fixed to each other. The first electrode 6 and the second electrode 8 are fixed while being spaced away from each other. The first electrode 6 and the second electrode 8 are made of an electrically conductive magnetic material such as iron, ferrite core and silicon steel. The magnet 7 is, for example, a permanent magnet. Instead of using such a permanent magnet, however, the first electrode 6 may serve both as the magnet and as the electrode.

The attracting portion 10 is provided to fill the space between the first electrode 6 and the second electrode 8 and interposed between the first electrode 6 and the second electrode 8. A distance X1 between the first electrode 6 and the wall portion 8b of the second electrode 8 is larger than the dimension of the conductive substance contained in the lubricating oil. For example, the conductive substance has a dimension of approximately 1.0 μm to 100 μm, and the distance X1 is preferably just large enough to prevent a short circuit from occurring due to iron powder produced by initial wear. In the embodiment illustrated, the magnet 7 is in contact with the first electrode 6 and surrounded by the attracting portion 10. The attracting portion 10 is made of an insulating non-magnetic material, for example, a resin. The magnet 7 forms a magnetic flux line between the first electrode 6 and the second electrode 8. Thus, the conductive substance contained in the lubricating oil is gathered to the vicinity of the attracting portion 10.

The sensor 5 includes the separate magnet 64B separate from the second electrode 8 (see FIG. 1).

The sensor 5 may be alternatively positioned, for example, inside the casing 21 but can be at any position within the space containing therein the lubricating oil in the mechanism 1. The separate magnet 64B is disposed at a position in the space S most spaced apart from the sensor 5. Accordingly, the separate magnet 64B is disposed at a position corresponding to that of the sensor 5. For example, it may be positioned inside the casing 21 but can be at any position within the space containing therein the lubricating oil in the mechanism 1.

The separate magnet 64B forms a magnetic flux line in the space S (see FIG. 1). Thus, the conductive abrasion powder contained in the lubricating oil is attracted onto the separate magnet 64B. Since the separate magnet 64B is exposed in the space S, the conductive abrasion powder contained in the lubricating oil is attracted onto the separate magnet 64B and also attracted by the magnet 7 onto the attracting portion (insulator) 10. As a result, the amount of the conductive abrasion powder attracted onto the attracting portion 10 is smaller than in the arrangement without the separate magnet 64B.

The separate magnet 64B has such an attractive force as to keep the conductive abrasion powder attracted thereto against the flow of the lubricating oil produced by operation of the speed reducer 2 or the like. The separate magnet 64B has such a magnetic force strength or a surface area as to reduce, by a predetermined amount, the amount of the conductive abrasion powder attracted onto the attracting portion 10 by the magnet 7. The separate magnet 64B may be alternatively formed of a material other than a magnet, capable of attracting the conductive abrasion powder.

In the embodiment shown in FIGS. 2A to 2B, the attraction portion 10 has a protrusion 10a formed integrally with the attracting portion 10. That is, the protrusion 10a and the attracting portion 10 form a one-piece structure. Therefore, similarly to the attracting portion 10, the protrusion 10a is made of an insulating non-magnetic material, for example, a resin. Alternatively, the attracting portion 10 and the protrusion 10a may be separate members from each other. In the sectional view of FIG. 2B, the protrusion 10a has a width substantially equal to the distance X1 between the first electrode 6 and the wall portion 8b of the second electrode 8. When seen from above the top surface of the sensor 5, the protrusion 10a has an annular shape and is formed to entirely surround the first electrode 6.

The first electrode 6 and the second electrode 8 are respectively connected to output lines (not shown) and electrically connected to a sensing unit 50 (see FIG. 1) via the output lines.

The sensing unit 50 is configured to sense a change in electrical resistance between the first electrode 6 and the second electrode 8. The sensing unit 50 includes a sensor drive circuit for predicting a failure of the parts constituting the mechanism 1 based on, for example, a change in electrical resistance caused by the gathering of the conductive substance in the vicinity of the attracting portion 10. If the conductive substance contained in the lubricating oil within the detection region is gathered in the vicinity of the attracting portion 10, this causes a drop in electrical resistance (or a short circuit) between the first electrode 6 and the second electrode 8 to which voltage is being applied, resulting in a change in output level of the output lines. The sensing unit 50 senses such a change in electrical resistance, thereby predicting a failure of the parts constituting the mechanism 1.

The drop in electrical resistance may be indicated by an ON signal and an OFF signal corresponding to electrical disconnection and connection. The sensing unit 50 may sense two states of electrical disconnection and connection (this operation may be hereinafter referred to as "digital sensing"). The sensing unit 50 may be connected to a higher-level control device (not shown) such as a manipulator in a wired or wireless manner. The higher-level control device may be configured to, upon reception of a signal from the sensing unit 50, issue an alert for demanding maintenance of, for example, the speed reducer 2 with a predetermined notifying unit (for example, a display or voice output device).

In the sensor 5 of the present embodiment, the separate magnet 64B may have an increased magnetic force or an increased surface area which increases the amount of the conductive abrasion powder that can be attracted onto the separate magnet 64B. An increased amount of the conductive abrasion powder that can be attracted onto the separate magnet 64B produces the same effect in the sensor 5 as produced by a larger creepage distance between the first electrode 6 and the second electrode 8, which results in a smaller amount of the conductive abrasion powder attracted onto the attracting portion 10.

In other words, when the magnetic force of the separate magnet 64B is increased or the surface area of the separate magnet 64B is increased, a larger amount of conductive abrasion powder can be attracted onto the attracting portion 10 before the resistance between the first electrode 6 and the second electrode 8 drops to a threshold value or before a short circuit occurs.

Conversely, when the magnetic force of the separate magnet 64B is reduced or the surface area of the separate magnet 64B is reduced, so as to reduce the amount of the conductive abrasion powder that can be attracted onto the separate magnet 64B, such a reduced amount produces the same effect as produced by a smaller creepage distance between the first electrode 6 and the second electrode 8, which results in a larger amount of the conductive abrasion powder attracted onto the attracting portion 10. In this case, it is possible to omit the separate magnet 64B. This is an option of the attractive power for a reduced magnetic force of the separate magnet. In other words, when the magnetic force of the separate magnet 64B is reduced or the surface area of the separate magnet 64B is reduced, a smaller amount of conductive abrasion powder can be attracted onto the attracting portion 10 before the resistance between the first electrode 6 and the second electrode 8 drops to a threshold value or before a short circuit occurs.

Accordingly, with the sensor 5 related to the present embodiment, even when the speed reducer 2 has a further larger size and thus produces an increased amount of initial abrasion powder, the sensor 5 can reliably sense the failure of the speed reducer 2 without being affected by the increased amount of initial abrasion powder. As described above, the sensor 5 can reliably sense the failure of the speed reducer 2 with different sensitivities by selecting appropriate one of the separate magnets 64B having different magnetic forces or shapes, without changing the sensor 5 and also without affecting the other constituents.

In the present embodiment, the abrasion powder is attracted onto the separate magnet 64B which is selected in accordance with the predicted amount of production of the conductive abrasion powder and spaced apart from the attracting portion 10 in the detection region. Since the separate magnet 64B attracts the abrasion powder, it is possible to reduce the amount of abrasion powder attracted between the first electrode 6 and the second electrode 8, and thus set the sensitivity of the sensor 5 at a predetermined level.

In the present embodiment, the separate magnet 64B serves as a sensitivity adjusting unit for adjusting attraction of conductive abrasion powder onto the attracting portion 10 to change the sensitivity of the sensor 5. The sensitivity adjusting unit of the present embodiment is capable of adjusting the amount of the conductive abrasion powder to be attracted onto the attracting portion 10 between the first electrode 6 and the second electrode 8. Specifically, the separate magnet 64B adjusts the attractive power for attracting the conductive abrasion powder. More specifically, the amount of the conductive abrasion powder that can be attracted onto the separate magnet 64B is adjusted by (1-i) adjusting the strength of the magnetic force of the separate magnet 64B, or (1-ii) increasing or reducing the surface area of the separate magnet 64B, and (2) increasing or reducing the thickness of a non-magnetic layer formed on the surface of the separate magnet 64B. Further, the sensitivity adjusting unit includes a plurality of separate magnets 64B having different attractive powers for attracting the conductive abrasion powder.

In this way, the sensor 5 relating to the present embodiment has a group of separate magnets 64B having different attractive powers. One of the separate magnets 64B is selected and disposed in the space S. In other words, the plurality of separate magnets 64B having different attractive powers constitute the sensitivity adjusting unit.

In the present embodiment, the separate magnet 64B may be installed for collecting iron powder produced by initial wear, thereby collecting such iron powder present in an excessive amount. This reduces the amount of the iron powder produced by initial wear and adhered to the attracting portion 10 of the sensor 5, making it possible to prevent malfunction due to such iron powder. Accordingly, it is not necessary to enlarge the gap length between the first electrode 6 and the second electrode 8 in the sensor 5. On the other hand, the amount of the abrasion powder produced at the occurrence of a failure of the speed reducer 2 is large beyond comparison with the amount of the iron powder produced by initial wear, and therefore, the performance of the sensor 5 in failure prediction is not affected. The sensor 5 is thus capable of reliable failure prediction.

Figure 3:
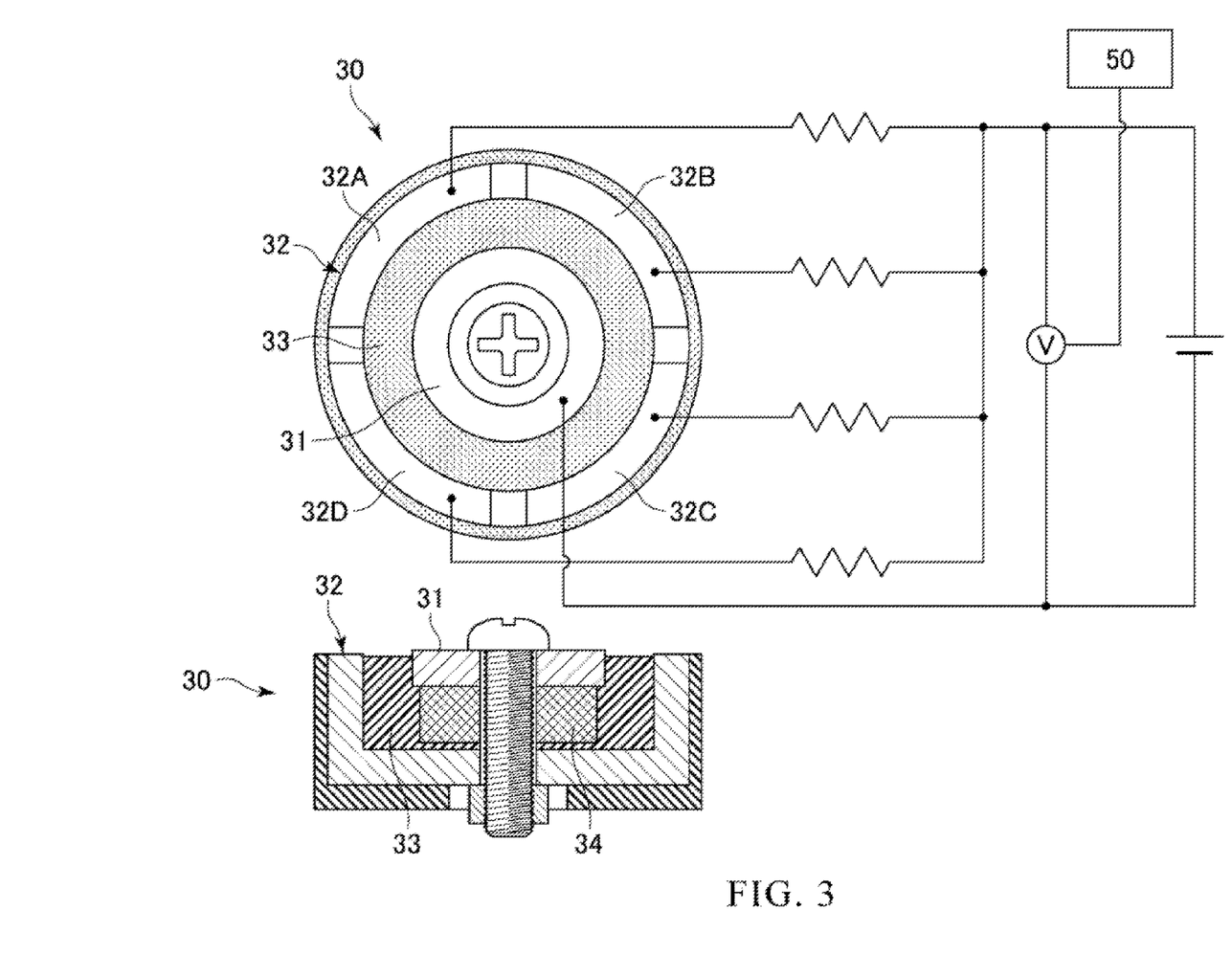
FIG. 3 is used to illustrate a sensor relating to a second embodiment of the present invention.

The following describes a second embodiment of the sensor relating to the present invention with reference to the drawings. FIG. 3 is used to illustrate the sensor relating to the second embodiment. The sensor 30 relating to the second embodiment is configured to sense the amount of a conductive substance contained in a lubricating oil, similarly to the sensor 5 relating to the first embodiment described above.

The sensor 30 has a substantially columnar outer shape and includes a plurality of detecting units and a sensing unit 50 configured to output a signal when the detecting units experience a change in electrical resistance. More specifically, the sensor 30 includes a center electrode 31, a plurality of outer electrodes 32, an attracting portion 33 disposed between the center electrode 31 and the outer electrodes 32, a magnet 34, and a separate magnet 64B (see FIG. 1). The outer electrodes 32 are insulated from each other. Each of the detecting units is constituted by a pair of electrodes and the attracting portion 33 disposed between the electrodes. The pair of electrodes includes the center electrode 31 and one of the outer electrodes 32.

In the embodiment illustrated, the sensor 30 includes outer electrodes 32A, 32B, 32C, and 32D, and four detecting units are formed in the sensor 30. There are no particular limitations on the number of the outer electrodes 32 and the number of the detecting units. The magnet 34 of the sensor 30 forms a magnetic flux line between the paired electrodes, so that a conductive substance contained in a lubricating oil is attracted onto the attracting portion 33. When the conductive substance is gathered in the vicinity of the attracting portion 33 in this manner, the detecting units experience a change in electrical resistance. While no conductive particles are attracted, the detecting units exhibit the same electrical resistance.

The center electrode 31 and the outer electrodes 32 are respectively connected to output lines, and each detecting unit is electrically connected to the sensing unit 50 via a corresponding one of the output lines. In this embodiment, the detecting units are connected in parallel to each other, and voltage is applied by the same voltage source between the center electrode 31 and each of the outer electrodes 32. The sensing unit 50 outputs a signal if a designated number of detecting units experience a change in electrical resistance. For example, the sensing unit 50 may be configured to output a signal to a higher-level control device such as a manipulator when two or more of the detecting units experience a drop in electrical resistance, or configured to output a signal when all of the detecting units experience a drop in electrical resistance.

As described above, the sensor 30 includes the plurality of detecting units, and the sensing unit 50 outputs a signal when a designated number of detecting units experience a drop in electrical resistance. In this way, the sensing unit 50 can be configured to output no signal when just one of the detecting units experiences a change in electrical resistance caused by a large-diameter conductive piece. Accordingly, the sensor can be prevented from operating unexpectedly due to a large-diameter conductive piece. Furthermore, in the sensor 30, the sensing unit 50 can be configured to output a signal under a designated condition. Therefore, the single sensor 30 can be configured to output a signal in a timely and optimal manner for individual users, who have different requests for failure prediction timing.

While no conductive particles are attracted, the detecting units exhibit the same electrical resistance. This can lower the voltage to be applied to the sensor 30.

The detecting units are connected in parallel to each other. This can lower the voltage applied between the paired electrodes in each detecting unit.

In the present embodiment, the separate magnet 64B may be installed for collecting iron powder produced by initial wear, thereby collecting such iron powder present in an excessive amount. This reduces the amount of the iron powder produced by initial wear and adhered to the attracting portion 33 of the sensor 30, making it possible to prevent malfunction due to such iron powder. Accordingly, it is not necessary to enlarge the gap length between the first electrode (inner electrode) 31 and the second electrode (outer electrode) 32 in the sensor 30. On the other hand, the amount of the abrasion powder produced at the occurrence of a failure of the speed reducer 2 is large beyond comparison with the amount of the iron powder produced by initial wear, and therefore, the performance of the sensor 30 in failure prediction is not affected. The sensor 5 is thus capable of reliable failure prediction.

Figure 4:
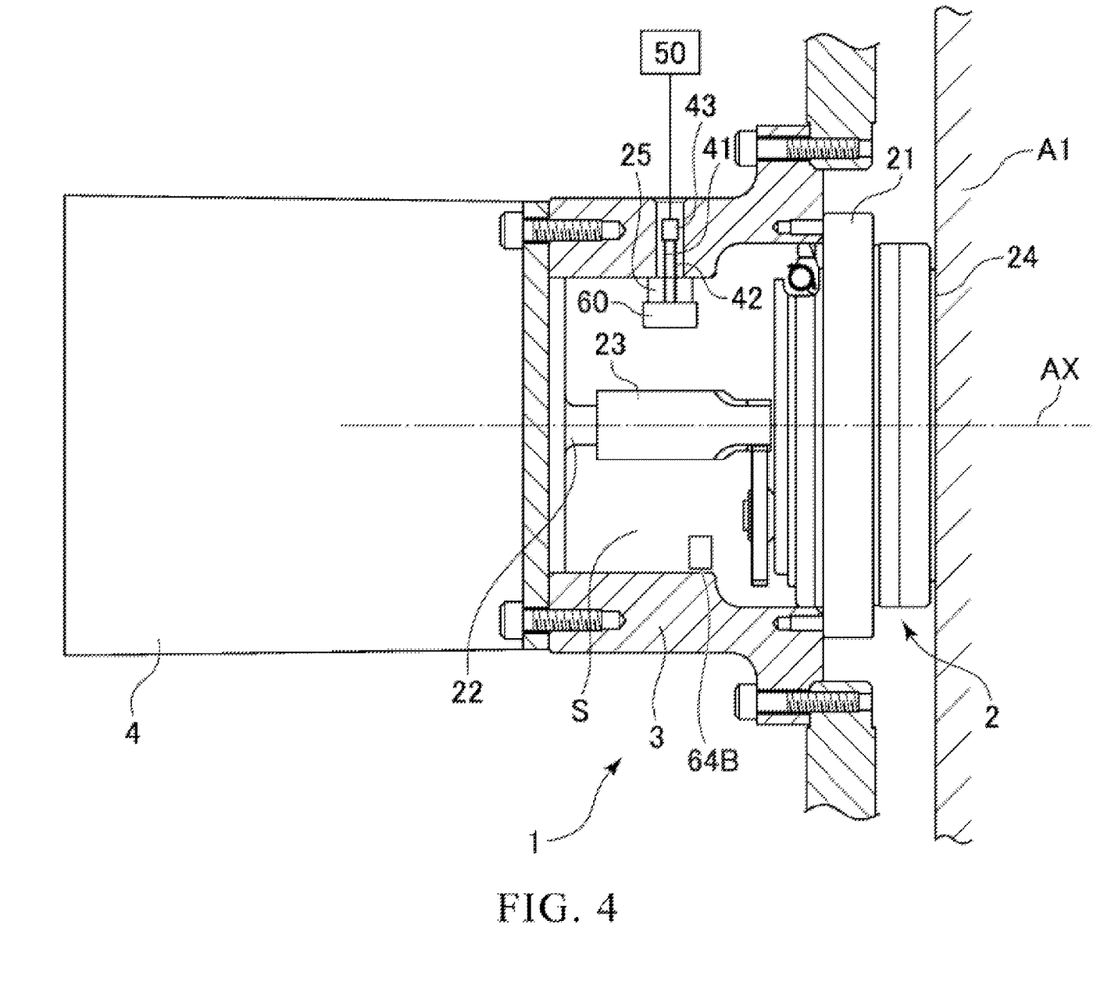
FIG. 4 is a sectional view showing one example of a mechanical device including a sensor relating to a third embodiment of the present invention.
Figure 5:
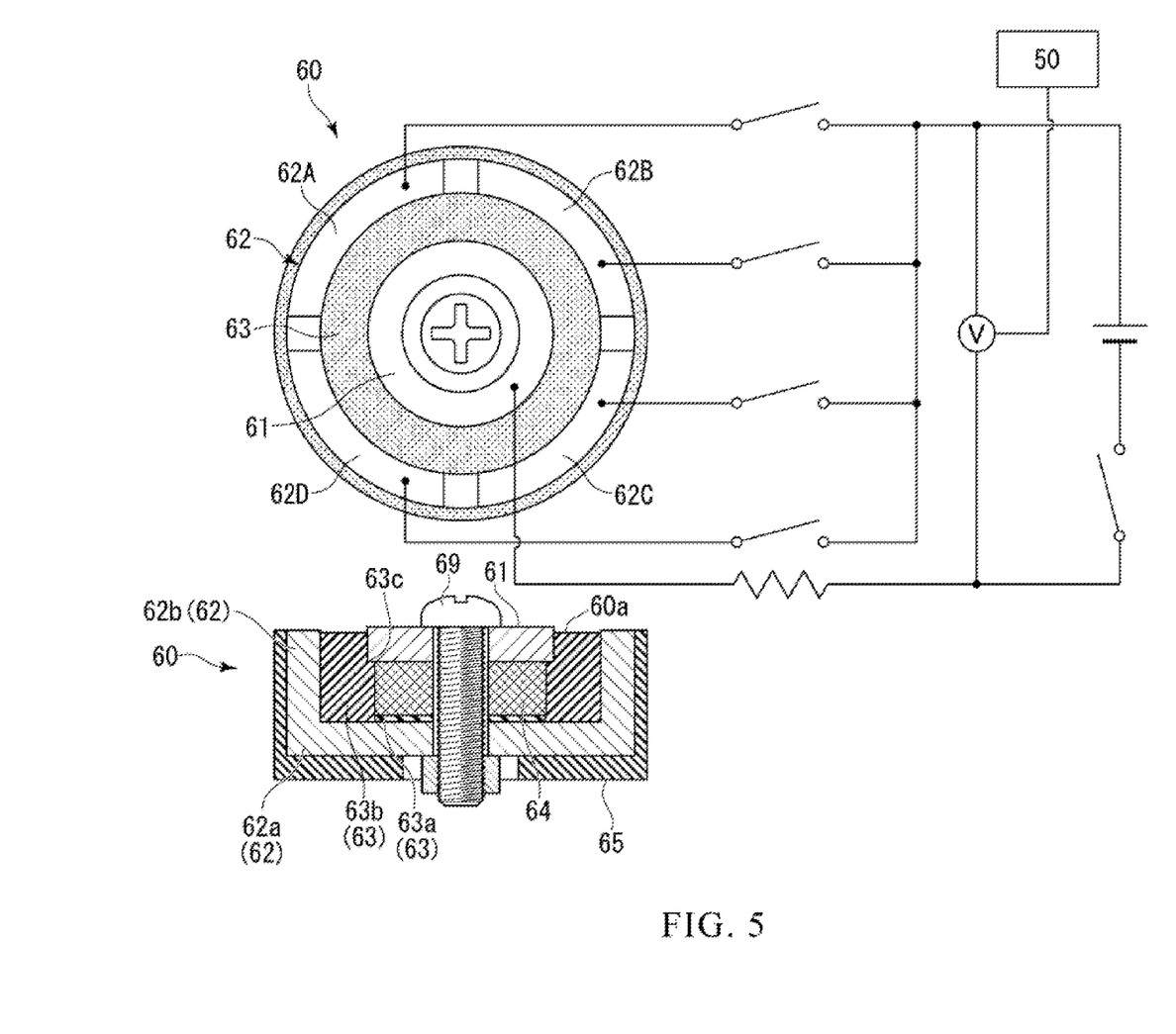
FIG. 5 is used to illustrate the sensor relating to the third embodiment of the present invention.

The following describes a third embodiment of the sensor relating to the present invention with reference to the drawings. FIG. 4 is a sectional view showing one example of a mechanism 1 including a sensor 60 relating to one embodiment of the present invention. FIG. 5 is used to illustrate the sensor relating to the third embodiment.

As shown in FIG. 5, the sensor 60 relating to the present embodiment has a substantially columnar outer shape and includes a first electrode (one example of the inner electrode recited in the claims) 61, a magnet 64 (one example of the first magnet recited in the claims), a second electrode (one example of the outer electrode recited in the claims) 62, a fastening member (fastening portion) 69, an attracting portion (a first attracting portion, one example of the insulator) 63 and a casing 65. When seen from above the top surface of the sensor 60, the first electrode 61 has a circular shape and is positioned at the center of the sensor 60. The second electrode 62 is a bottomed tubular member and has a bottom portion 62*a* extending substantially parallel to the first electrode 61 and a wall portion (tubular portion) 62*b* continuous with the bottom portion 62*a* and extending substantially perpendicularly to the bottom portion 62*a*. The first electrode 61 is positioned in the opening of the second electrode 62.

The magnet 64 has a substantially columnar (substantially disk-like) shape and is positioned between the first electrode 61 and the bottom portion 62*a* of the second electrode 62. The first electrode 61, the magnet 64, and the bottom portion 62*a* of the second electrode 62 each have therein a through hole, through which the fastening member 69 (a bolt in the illustrated embodiment) is inserted. The fastening member 69 is inserted through the through holes, so that the first electrode 61, the magnet 64, and the second electrode 62 are fixed to each other. The magnet 64 is smaller in outer diameter than the second electrode 62.

The first electrode 61 and the second electrode 62 are fixed while being spaced away from each other. The first electrode 61 and the second electrode 62 are made of an electrically conductive magnetic material such as iron, ferrite core and silicon steel. The magnet 64 is, for example, a permanent magnet. Instead of using such a permanent magnet, however, the first electrode 61 may serve both as the magnet and as the electrode.

The attracting portion 63 is provided to fill the space between the first electrode 61 and the second electrode 62 and interposed between the first electrode 61 and the second electrode 62. The attracting portion 63 has a bottom portion 63*a* extending along the bottom portion 62*a* of the second electrode 62 and a tubular portion 63*b* extending along the wall portion 62*b* of the second electrode 62. The bottom portion 63*a* and the tubular portion 63*b* are separate members. The bottom portion 63*a* is shaped like a sheet.

The bottom portion 63*a* of the attracting portion 63 can be, for example, an insulating paper sheet having a thickness of 0.05 to 1 mm. The bottom portion 63*a* of the attracting portion 63 can be a circular paper sheet having an outer diameter substantially the same as the inner diameter of the tubular portion 63*b*. Alternatively, the bottom portion 63*a* can be a circular paper sheet having an outer diameter larger than the inner diameter of the tubular portion 63*b*. In this case, the bottom portion 63*a* can be a circular paper sheet having an outer diameter smaller than the outer diameter of the tubular portion 63*b*. Alternatively, the bottom portion 63*a* can be a circular paper sheet having an outer diameter same as the outer diameter of the tubular portion 63*b*.

On the inner surface of the tubular portion 63*b* of the attracting portion 63, a step 63*c* is formed. In the tubular portion 63*b* of the attracting portion 63, the portion on the first electrode 61 side with respect to the step 63*c* has an inner diameter equal to the outer diameter of the first electrode 61. In the tubular portion 63*b* of the attracting portion 63, the portion on the magnet 64 side with respect to the step 63*c* has an inner diameter equal to the outer diameter of the magnet 64.

The thickness of the end of the tubular portion 63*b* of the attracting portion 63, in other words, the distance X1 between the first electrode 61 and the wall portion 62*b* of the second electrode 62 is larger than the dimension of the conductive substance contained in the lubricating oil. For example, the conductive substance has a dimension of approximately 1.0 µm to 100 µm, and the thickness of the end of the tubular portion 63*b* of the attracting portion 63 is preferably just large enough to prevent a short circuit from occurring due to iron powder produced by initial wear. In the embodiment illustrated, the magnet 64 is in contact with the first electrode 61 and surrounded by the attracting portion 63.

The attracting portion 63 is made of an insulating non-magnetic material, for example, a resin. The magnet 64 forms a magnetic flux line between the first electrode 61 and the second electrode 62. Thus, the conductive substance contained in the lubricating oil is gathered to the vicinity of the attracting portion 63.

In the sensor 60 relating to the present embodiment, a sensing plane 60*a* denotes the plane connecting the first electrode 61 and the end of the second electrode 62. In other words, on the sensing plane 60*a*, conductive abrasion powder is attracted between the first electrode 61 and the second electrode 62 by the magnetic flux line, so that the first electrode 61 and the second electrode 62 are electrically connected. This causes a change in resistance between the first electrode 61 and the second electrode 62, which is to be detected.

As the creepage distance between the first electrode 61 and the second electrode 62 increases, a larger amount of conductive abrasion powder can be attracted before the resistance between the first electrode 61 and the second electrode 62 drops to a threshold value or before a short circuit occurs. As the creepage distance between the first electrode 61 and the second electrode 62 decreases, a smaller amount of conductive abrasion powder can be attracted before the resistance between the first electrode 61 and the second electrode 62 drops to a threshold value or before a short circuit occurs.

The sensor 60 relating to the present embodiment has a sensitivity adjusting unit for adjusting the attraction of the conductive abrasion powder to change the sensitivity. In the present embodiment, the sensitivity adjusting unit is formed of a separate attracting portion (a second attracting portion, a separate magnet) 64B (see FIG. 4). Further, in the present embodiment, the sensitivity adjusting unit can be selected from a group of separate attracting portions (separate magnets) 64B having different attracting powers.

The attractive power of the separate attracting portion (separate magnet) 64B of the present embodiment can be selected to adjust the amount of the conductive abrasion powder to be attracted between the first electrode 61 and the second electrode 62. In this way, the amount of the conductive abrasion powder to be attracted between the first electrode 61 and the second electrode 62 can be selected from among a plurality of values by making a selection in the separate attracting portion (separate magnet) 64B as the sensitivity adjusting unit.

The mechanism 1 shown in FIG. 4 is the same as that of the first embodiment shown in FIG. 1. In FIG. 4, the position of the sensor 60 within the detection region may be, for example, inside the casing 21, but it can be disposed at any position within the space containing therein the lubricating oil in the mechanism 1. The separate magnet 64B can be disposed at any position in the space S spaced apart from the sensor 60. In the present embodiment, the position of the separate magnet 64B is slightly closer to the sensor 60 than in the mechanism 1 shown in FIG. 1.

The sensor 60 relating to the present embodiment can be assembled in the following manner.

To start with, the outer electrode 62 is placed within the casing 65. Subsequently, the bottom portion 63*a* of the attracting portion 63 is positioned on the bottom portion 62*a* of the outer electrode 62. Following this, the tubular portion 63*b* of the attracting portion 63 having a selected height is inserted into the outer electrode 62. Subsequently, the magnet 64 is inserted into the tubular portion 63*b*, and the center electrode (inner electrode) 61 is further inserted. At this stage, the fastening member 69 is inserted and fixedly fastened. In this way, the sensor 60 is assembled.

Having the sensitivity adjusting unit, the sensor 60 relating to the present embodiment is capable of setting the sensitivity at a predetermined level. Specifically, when a large amount of conductive abrasion powder is expected to be produced, the sensitivity adjusting unit can be selected such that a larger creepage distance to attract the abrasion powder can be obtained between the electrode 61 and the electrode 62 to set the sensitivity of the sensor 60 at a predetermined level. In addition, when a small amount of conductive abrasion powder is expected to be produced, the sensitivity adjusting unit can be selected such that a smaller creepage distance to attract the abrasion powder can be obtained between the electrode 61 and the electrode 62 to set the sensitivity of the sensor 60 at a predetermined level. In this way, the sensor 60 can reliably sense a failure of the speed reducer 2 without being affected by the increased amount of initial abrasion powder produced by the speed reducer 2.

Speed reducers of different models (sizes) may produce different amounts of iron powder (abrasion powder) during the initial wear period. In the case of large speed reducers, a large amount of iron powder is produced by initial wear, and such iron powder may fill the electrical gap in the sensor between the electrodes 61 and 62. If such is the case, the sensor may react and erroneously operate. Therefore, the electrical gap in the sensor needs to be determined considering the model of the speed reducer, but this requirement may disadvantageously result in a larger sensor size in the diameter direction. To address this issue, the sensor 60 relating to the present embodiment has a sensitivity adjusting unit, which is formed of the separate attracting portion (separate magnet) 64B having different attractive powers. This configuration allows the sensor 60 to maintain the size. The separate attracting portion 64B may alternatively be formed of a filter or the like instead of a magnet.

The individual features of the above-described embodiments of the present invention can be combined as appropriate.

What is claimed is:
1. A sensor comprising:
a first electrode;
a second electrode;
a first attracting portion positioned between the first electrode and the second electrode, the first attracting portion configured to receive conductive abrasion powder contained in a detection region and attracted onto the first attracting portion;
a sensing unit configured to sense a change in electrical resistance between the first electrode and the second electrode caused by the conductive abrasion powder attracted onto the first attracting portion;
at least one second attracting portion positioned within the detection region and configured to attract the conductive abrasion powder contained in the detection region, and
a sensitivity adjusting unit for adjusting attraction of the conductive abrasion powder with respect to the first attracting portion to adjust a detection sensitivity of the sensing unit, wherein the first attracting portion is made of an insulating material and is arranged to fill a space between the first electrode and the second electrode, and attracts the conductive abrasion powder onto an outer surface of the first attracting portion by a magnetic force of a first magnet, wherein the at least one second attracting portion comprises a second magnet configured to attract the conductive abrasion powder, and wherein the sensitivity adjusting unit adjusts attraction of the conductive abrasion powder with respect to the first attracting portion by using the second magnet.

2. The sensor of claim 1, wherein the at least one second attracting portion is spaced apart from the first electrode, the second electrode, and the first attracting portion.

3. The sensor of claim 2, wherein the second magnet of the at least one second attracting portion is one of a plurality of second magnets having different attractive powers for attracting the conductive abrasion powder.

4. The sensor of claim 1, wherein the second magnet of the at least one second attracting portion is one of a plurality of second magnets having different attractive powers for attracting the conductive abrasion powder.

5. The sensor of claim 1, wherein the first attracting portion includes a protrusion that surrounds the first electrode, and wherein the conductive abrasion powder is attracted onto the surface of the protrusion of the first attracting portion by the magnetic force of the first magnet, and wherein the outer surface is the surface of the protrusion of the first attracting portion.

6. The sensor of claim 5, wherein the protrusion of the first attracting portion is integrally formed with the first attracting portion.

7. The sensor of claim 5, wherein the first attracting portion and the protrusion are formed as separate members from each other.

8. The sensor of claim 5, wherein the protrusion of the first attracting portion is made of an insulating non-magnetic material.

9. The sensor of claim 5, wherein, in a cross-sectional view of the sensor, the protrusion has a width substantially equal to a distance between the first electrode and a wall portion of the second electrode.

10. The sensor of claim 5, wherein, in a top elevational view of the sensor, the protrusion of the first attracting portion has an annular shape and is formed to entirely surround the first electrode.

11. The sensor of claim 5, wherein the outer surface is disposed along a plane that connects the first electrode and the second electrode, wherein, on the plane, the conductive abrasion powder is attracted between the first electrode and the second electrode by a magnetic flux line, so that the first electrode and the second electrode are electrically connected, which causes a change in resistance between the first electrode and the second electrode.

12. A sensor comprising:

an outer electrode shaped like a tube having a bottom portion;

an insulator arranged within the outer electrode, the insulator being an internal tube having a bottom portion;

a first magnet arranged within the insulator;

an inner electrode arranged within the insulator, the inner electrode being closer to an opening of the outer electrode in an axial direction than the first magnet is;

a sensing unit configured to sense attraction of conductive abrasion powder causing a change in electrical resistance between the outer electrode and the inner electrode; and a second magnet arranged outside the outer electrode and configured to attract the conductive abrasion powder, a sensitivity adjusting unit configured to adjust a detection sensitivity of the sensing unit, wherein the insulator is arranged to fill a space between the outer electrode and the inner electrode, and attracts the conductive abrasion powder onto a sensing plane of the insulator by a magnetic force of a first magnet, and wherein the sensitivity adjusts unit adjusting attraction of the conductive abrasion powder with respect to the insulator by using the second magnet to adjust the detection sensitivity of the sensing unit.

13. The sensor of claim 12, wherein the first magnet forms a magnetic flux line between the outer electrode and the inner electrode.

* * * * *